United States Patent [19]

Klabunde et al.

[11] Patent Number: 4,588,708

[45] Date of Patent: May 13, 1986

[54] BIMETALLIC SOLVATED METAL ATOM DISPERSED CATALYSTS

[75] Inventors: Kenneth J. Klabunde, Manhattan, Kans.; Yuzo Imizu, Kitami, Japan

[73] Assignee: Kansas State University Research Foundation, Manhattan, Kans.

[21] Appl. No.: 723,216

[22] Filed: Apr. 15, 1985

[51] Int. Cl.[4] .......................... B01J 23/24; B01J 21/12
[52] U.S. Cl. ...................................... 502/241; 502/74; 502/171; 502/324
[58] Field of Search ........................ 502/241, 324, 171

[56] References Cited

U.S. PATENT DOCUMENTS

| | | | |
|---|---|---|---|
| 2,793,241 | 5/1957 | Fawcett et al. | 502/241 X |
| 3,264,208 | 8/1966 | Plank et al. | 502/241 X |
| 3,264,226 | 8/1966 | Johnson | 502/241 X |
| 3,932,468 | 1/1976 | Kurkov | 502/171 X |

FOREIGN PATENT DOCUMENTS 5772  1/1980  Japan ................................. 502/324

OTHER PUBLICATIONS

Klabunde et al. (1978), *J. Catalysis*, 55:213–227.
Klabunde et al., *J. Molecular Catalysis*, (1983), 21:57–79.
Klabunde et al., *J. Am. Chem. Soc.*, (1976), 98:1021–1023.
J. Am. Chem. Soc., 106:2721–2722, (1984), by Klabunde et al.

*Primary Examiner*—Carl F. Dees

[57] ABSTRACT

Activated bimetallic heterogeneous catalysts are provided comprising a catalyst support having deposited thereon a solvated dispersion of cobalt and manganese. The manganese activates the catalytic activity of the cobalt.

10 Claims, No Drawings

BIMETALLIC SOLVATED METAL ATOM DISPERSED CATALYSTS

GRANT REFERENCE

Research leading to the present invention was supported in part by The National Science Foundation.

FIELD OF INVENTION, BACKGROUND AND PRIOR ART

The field of this invention is catalysts prepared from atomically-dispersed catalytic metals. More specifically, the invention is concerned with solvated metal atom dispersed catalysts, referred to as "SMAD" catalysts.

Dr. Kenneth J. Klabunde and associates have developed and published a procedure for forming solvated metal atom dispersions, and have demonstrated the utility of this procedure for depositing atomic dispersions of catalytic metals on catalyst supports. See, for example, Klabunde et al. (1976), *J. Am. Chem. Soc.* 98: 1021-1023; and Matsuo and Klabunde (1982), *J. Org. Chem.*, 47: 843-848.

SMAD monometallic catalysts have been prepared from a number of catalytic metals, including nickel, cobalt, iron, manganese, and chromium. In the 1976 paper cited above, it was suggested that the SMAD procedure might be useful for preparation of bimetallic particles. However, prior to the present invention, bimetallic SMAD catalysts are not known to have been prepared.

The work leading to the present invention was first reported by Klabunde and Imizu, named herein as co-inventors, in *J. Am. Chem. Soc.*, 106: 2721-2722 (1984). The importance of the manganese-cobalt SMAD catalyst described by Klabunde and Imizu has been recognized in a subsequent article in *Science*, 224: 1329-1330 (June, 1984).

SUMMARY OF INVENTION

The present invention is based on the discovery that manganese activates the catalytic activity of cobalt in bimetallic catalysts prepared from solvated metal atom dispersions. This discovery has made possible the preparation of a family of activated bimetallic heterogeneous SMAD catalysts. These catalysts comprise a compatible catalyst support having deposited thereon a solvated atom dispersion of cobalt and manganese. In reactions such as hydrogenation of unsaturated hydrocarbons, where a monometallic manganese SMAD catalyst has no significant catalytic activity, the catalytic activity of the cobalt can be increased by a factor of 100 compared to a corresponding monometallic cobalt SMAD catalyst. Such activation is believed to be a novel and heretofore unreported phenomenon. Doping of one catalytic metal by a second metal may result in selectivity differences for certain reactions but this is a different effect from that of potentiating catalytic activity. See, for example, Sinfelt et al. (1972), *J. Catal.*, 24: 283-296; and Sinfelt, *Science*, (1977) 195: 641.

DETAILED DESCRIPTION

An apparatus for preparing monometallic SMAD catalysts by the metal vapor method is described in Klabunde, et al. (1978), *J. Catal.*, 55: 213-227; and Klabunde, et al. (1979), *Inorg. Synth.*, 19: 59-86. Briefly, the apparatus comprises a vaccum flask provided with a jacket for liquid nitrogen cooling. The center of the flask is equipped with an electric crucible for vaporizing the metal, and with an inlet for the solvent. In the operation of the apparatus, the solvent vaporizes on entry, and then condenses on the inner walls of the flask together with the vaporized metal atoms. This condensation and cooling generates a frozen matrix of metal atoms and solvent which collects on the walls of the flask. When the SMAD procedure is being used to prepare a catalyst, particulate support material may be placed in the bottom of the flask where the condensate collects. Upon completion of the condensate formation, the liquid nitrogen cooling is discontinued. The flask can then be warmed to form a slurry of the catalyst support particles and the liquified solvated metal. As this contacting continues the solvated metal deposits on the support particles and forms the SMAD catalyst. Alternatively, solvated metal solution can be removed from the reactor and thereafter warmed and contacted with the catalyst support material in a slurry-type reactor.

For preparing the bimetallic catalysts, the SMAD apparatus will be equipped with two metal vaporization crucibles and two separate power supplies for independent control of the heating in each crucible. The rate of vaporization of the metals can thereby be individually controlled to achieve desired relative proportions of the two metals. The flow rate of the solvent is also controlled to achieve the desired relative proportions of metal to solvent. As the slurry of the catalyst support and the solvated metal atoms are warmed, the atom solvate matrix decomposes and the metal atoms deposit on the support, either atom by atom or in clusters. Deposition may occur on both the external and pore surfaces of a porous support material.

The solvent, which may be a hydrocarbon solvent, associates with the metal particles to provide pseudo-organometallic particles. Although the solvated metal incorporates carbonaceous fragments of the solvent, this does not poison catalytic action. Further, the incorporated organic fragments are believed to improve attachment of the metal particles to the catalyst support surfaces.

In preparing the bimetallic catalyst of the present invention, from 1 to 60 parts by weight of manganese may be covaporized and condensed with from 40 to 99 parts of cobalt. This will result in catalysts containing from 40 to 99 weight percent of atomically-dispersed cobalt together with from 60 to 1 percent of atomically-dispersed manganese (based on the total metal). In presently preferred embodiments, from 55 to 70 weight percent of cobalt are combined with 30 to 45 weight percent manganese. The cobalt and manganese are preferably in the form of high purity metals, such as a purity of 99.9% or higher.

As previously indicated, a number of different solvents can be usefully employed for solvating the metal atoms. Hydrocarbon solvents which are liquids at room temperature have been found to be effective for solvating the metal atoms. Such solvents include, alkanes, alkenes, aromatic and cyclic hydrocarbons. For example, pentane, hexane, toluene, xylene, and tetrahydrofuran are usually advantageous. For the purpose of the present invention, it appears that the best solvents are toluene, xylene, or tetrahydrofuran. Toluene is the prototype solvent employed in the experimental development and is believed to be desirable.

A wide variety of conventional catalyst supports can be employed. The support material is preferably in granular or particulate form. Both porous and non-porous support material can be used. Catalysts supports which can be employed for SMAD catalysts are described in Matsuo and Klabunde (1982), *J. Org. Chem.*, 47: 843-844. These catalysts supports include magnesium oxide (MgO), alumina ($Al_2O_3$), silica ($SiO_2$) and carbon. Other usable catalytic supports include natural and artificial zeolites. For the purpose of the present invention, acidic supports such as silica and alumina are believed to be preferred. Based on present information, silica is particularly effective. The support materials can be used in the standard commercial forms as supplied for use as catalytic support materials. The percent loading of the catalyst metals on the support is not highly critical. From 1 to 15 parts by weight of the catalyst metal may be combined per 100 parts of supports. A preferred loading is from about 2 to 10 parts of the metals per 100 parts support.

This invention is further illustrated by the following experimental examples.

EXPERIMENTAL EXAMPLES

A series of bimetallic cobalt/manganese SMAD catalysts were prepared with varying ratios of cobalt and manganese. SMAD catalysts were also prepared from Co and Mn individually. The procedure was as follows:

An apparatus similar to those described previously (*Inorg. Synth.*, 1979, 19:59-86), was constructed. However, the apparatus was modified to provide four water-cooled copper electrodes, two metal vaporization crucibles, and two separate power supplies. The heat to each crucible could thereby be separately controlled. In preparing the Co-Mn catalysts, the two metals were vaporized simultaneously as excess toluene solvent vapor was inletted (sequential vaporization of the two metals also worked satisfactorily). The liquid nitrogen cooled walls condensed the toluene and metal atoms into a frozen matrix. About 0.02-1.4 g of each metal and 100 mL of toluene were used in each experiment. The runs lasted about 2 hours.

After completion of the tri-deposition, the matrix was allowed to warm slowly to −95° C. whereupon it melted and formed a toluene-solvated metal atom solution. This solution was stirred and slowly warmed further in the presence of a powdered $SiO_2$ catalyst support (20 g, preheat treated at 500° C. for 3 h in dry air, cooled, and handled under pure nitrogen prior to and during transfer to the reaction chamber where it was placed under vacuum prior to the metal vapor reaction). During the warming period of about 2 h, the solution turned from dark red-brown to a clear solution. Major color change occurred in the −50° to −20° C. range, where most of the metal nucleation/deposition along with toluene reaction apparently occurred. After reaching room temperature the mixture was vacuum siphoned and placed under nitrogen in airless glassware. Toluene was removed under vacuum and the resultant dark powder placed in a reactor in the inert atmosphere box. The recovered catalyst was then outgassed at room temperature to less than $1 \times 10^{-5}$ torr and subsequently used without further treatment.

The series of catalysts prepared as described were employed in typical hydrocarbon catalysis reactions: (1) isomerization of 1-butene, hydrogenation of 1-butene, (3) hydrogenation of 1,3-butadiene, and (4) hydrogenolysis of cyclopropane. A flow system was assembled so that reagents in gas form could be circulated over small portions of the catalysts. The system was constructed so that the catalyst could be loaded under inert atmosphere, and its temperature could be maintained at a selected temperature. A typical operating temperature employed was 0° C. The apparatus was constructed so that gas samples could be extracted for analysis. The results of the tests are summarized below in Table A.

TABLE A

Initial Reaction Rates for 1-Butene Isomerization, 1-Butene Hydrogenation, and 1,3-Butadiene Hydrogenation over Bimetallic SMAD Catalysts Compared with Corresponding Monometallic Catalysts

| Catalyst[b] | Atom %[c] | Initial Rates, molecule/(M atom s) | | |
|---|---|---|---|---|
| | | Isom 1-$C_4$'[d] | Hydrog 1-$C_4$'[e] | Hydrog 1,3-$C_4$'[f] |
| 4.1% Co—0.1% Mn | 2.5 | 0.018 | 0.35[g] | 0.18 (0.57)[h] |
| 3.6% Co—0.8% Mn | 19.3 | 0.084 | 0.45[g] | |
| 2.0% Co—1.1% Mn | 37.6 | 0.018 | 0.79[g] | |
| 3.3% Co—2.6% Mn | 45.8 | 0.024 | 0.53[g] | |
| 3.4% Co—3.3% Mn | 51.0 | 0.021 | 0.50[g] | 0.083 (0.56)[h] |
| 1.7% Co—5.1% Mn | 76.3 | 0.016 | 0.016 | 0.0053 (0.95)[h] |
| 2.3% Co | | 0.0063 | 0.029 | 0.012 (0.98)[h] |
| 3.4% Mn | | 0 | 0.000013 | 0.00030 (1.0)[h] |

[a]Based on 100% Co dispersion neglecting second metal contribution.
[b]$SiO_2$ support, wt %
[c]Atom % of second metal, not including support.
[d]$P_{rea}$ = 30 torr, without $H_2$, 253K.
[e]$H_2$/HC = 1.67, $P_{tot}$ = 80 torr, 213K.
[f]$H_2$/HC = 2, $P_{tot}$ = 60 torr, 273K.
[g]The rate was controlled by diffusion.
[h]Ratios of butene to (butenes + butane).

As shown by the data of Table A, Mn alone was very inactive as a catalyst. Remarkably, however, Mn substantially increased the catalytic activity of the Co/$SiO_2$ system. Only 2.5 atom % Mn increased the activity for hydrogenation by $10^2$. Even higher activities were obtained by adding more Mn. The data shows that the activity of Mn/$SiO_2$ is $10^2$ lower than that of Co/$SiO_2$, and at least $10^4$ lower than Co/Mn/$SiO_2$.

The significance of the foregoing data can be further appreciated in relation to commercial hydrogenation catalysts which are generally 2 to 10-fold less active than monometallic cobalt SMAD catalysts. The optimum bimetallic Co-Mn SMAD catalyst tested was therefore about 200-1,000 more active than commercial hydrogenation catalysts. The isomerization of 1-butene was 3 to 4-fold more rapid with the Co-Mn SMAD catalyst than with the Co-SMAD catalyst, which, however, was about 2-fold more active for such isomerizations than conventional catalysts. It follows, therefore, that the Co-Mn SMAD catalysts were about eight times more active for this typical isomerization reaction than conventional catalysts.

It was also found that for a typical hydrogenolysis reaction (carbon-carbon bond cleavage) the Co-Mn SMAD catalyst was about 15-fold more active than the Co-SMAD catalyst, which was about 2 to 5-fold more active than conventional catalysts. This means that the Co-Mn SMAD catalyst was about 10 to 75-fold more active than conventional catalysts for the carbon-carbon bond cleavage reaction. This comparison (not included in Table A) involved the hydrogenolysis of cyclopropane to normal propane.

Catalyst life was studied on a preliminary basis by repeating the 1-butene hydrogenations. After hydrogenation cycles such that each site was used 470 times or over, no sign of deactivation was noted.

We claim:

1. An activated bimetallic heterogeneous catalyst, comprising a catalyst support having deposited thereon a slovated dispersion of cobalt and manganese, said dispersion having been formed by co-condensation of cobalt, manganese, and organic solvent vapors, said catalyst containing from 40 to 99 weight percent of atomically-dispersed cobalt together with from 60 to 1 percent of atomically-dispersed manganese based on the total weight of the cobalt and manganese.

2. An activated bimetallic heterogeneous catalyst, comprising a catalyst support having deposited thereon a solvated dispersion of cobalt and manganese, said dispersion having been formed by co-condensation of cobalt, manganese, and organic solvent vapors, said catalyst containing from 55 to 70 weight percent of atomically-dispersed cobalt together with from 45 to 30 percent of atomically-dispersed manganese based on the total weight of the cobalt and manganese.

3. The catalyst of claim 1 in which said atomic dispersion of cobalt and manganese was solvated with a solvent selected from the group consisting of toluene, xylene, and tetrahydrofuran.

4. The catalyst of claim 2 in which said atomic dispersion of cobalt and manganese was solvated with a solvent selected from the group consisting of toluene, xylene, and tetrahydrofuran.

5. The catalyst of claim 1 in which said catalyst support is selected from the group consisting of silica and alumina.

6. The catalyst of claim 2 in which said catalyst support is selected from the group consisting of silica and alumina.

7. An activated bimetallic heterogeneous catalyst, comprising a catalyst support having deposited thereon a solvated dispersion of cobalt and manganese, said dispersion having been formed by co-condensation of cobalt, manganese, and organic solvent vapors said catalyst support being selected from the group consisting of silica and alumina, said catalyst containing from 55 to 70 weight percent of atomically dispersed cobalt, together with 45 to 30 weight percent of atomically-dispersed manganese, said dispersion of cobalt and manganese having been solvated with a solvent selected from the group consisting of toluene, xylene, and tetrahydrofuran.

8. The catalyst of claim 7 in which said catalyst support is silica and said solvent is toluene.

9. The catalyst of claim 7 wherein from 2 to 10 parts by weight of said cobalt and manganese are present per 100 parts of said silica support.

10. The catalyst of claim 8 wherein from 2 to 10 parts by weight of said cobalt and manganese are present per 100 parts of said silica support.

* * * * *